United States Patent [19]

Berger et al.

[11] 4,088,761
[45] May 9, 1978

[54] 3-[(1,3-DITHIIN-5-YL)-ACETAMIDO]-CEPHALOSPORINS AND ANTIBACTERIAL COMPOSITIONS CONTAINING THEM

[75] Inventors: Christian Berger, Plessis Robinson; Daniel Farge, Thiais; Claude Moutonnier, Plessis Robinson, all of France

[73] Assignee: Rhone-Poulenc Industries, Paris, France

[21] Appl. No.: 759,906

[22] Filed: Jan. 17, 1977

[30] Foreign Application Priority Data

Jan. 19, 1976 France ................................. 76 01230

[51] Int. Cl.² .................. C07D 501/36; A61K 31/545
[52] U.S. Cl. ...................................... 424/246; 544/30; 544/27
[58] Field of Search ..................... 260/243 C; 424/246

[56] References Cited
U.S. PATENT DOCUMENTS 4,007,176  2/1977  Berger et al. .................... 260/243 C Primary Examiner—Nicholas S. Rizzo
Attorney, Agent, or Firm—Stevens, Davis, Miller & Mosher

[57] ABSTRACT

The invention provides novel cephalosporins of the formula:

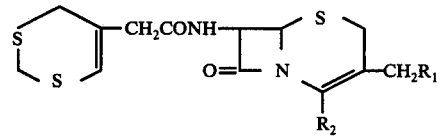

in which $R_1$ represents acetoxy, (5-methyl-1,3,4-thiadiazol-2-yl)-thio, (1-methyl-tetrazol-5-yl)-thio or [1-(2-hydroxyethyl)-tetrazol-5-yl]-thio and $R_2$ represents carboxyl, or $R_1$ represents pyridinio and $R_2$ the carboxylato ion, and, when $R_2$ represents carboxyl, their metal salts and addition salts with nitrogen-containing bases, which have useful antibacterial properties.

6 Claims, No Drawings

3-[(1,3-DITHIIN-5-YL)-ACETAMIDO]-CEPHALOSPORINS AND ANTIBACTERIAL COMPOSITIONS CONTAINING THEM

The present invention provides as new compounds the cephalosporin derivatives of the formula:

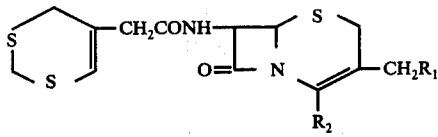

in which $R_1$ represents acetoxy, (5-methyl-1,3,4-thiadiazol-2yl)-thio, (1-methyl-tetrazol-5-yl)-thio or [1-(2-hydroxyethyl)-tetrazol-5-yl]-thio and $R_2$ represents carboxyl, or $R_1$ represents pyridinio and $R_2$ represents the carboxylato ion, and, where $R_2$ represents carboxyl, their metal salts and addition salts with nitrogen-containing bases.

According to a feature of the invention, the compounds of the formula (I) are obtained by reaction of the acid of the formula:

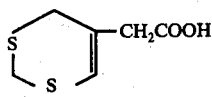

or of a reactive derivative of this acid, such as a halide, the anhydride or a mixed anhydride, with a cephalosporin of the formula:

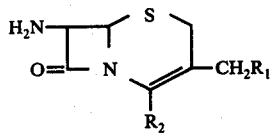

in which $R_1$ and $R_2$ are as defined above, or, when $R_2$ is carboxyl, a derivative of such a compound in which the carboxyl group is protected beforehand by a group which is easily removable, such as the tertiary butyl radical, and, after the reaction removing any such easily removable group.

In general, the condensation is carried out in an organic solvent such as dimethylformamide, in the presence of a condensation agent such as dicyclohexylcarbodiimide, at a temperature of between 0° and 40° C, after which any protective group of the acid function is removed, for example by scission in an acid medium.

If the acid of the formula (II) is used in the form of a halide, of the anhydride or of a mixed anhydride, the protection of the acid function of the product of the general formula (III) is not necessary. In general, the condensation is carried out in an organic solvent such as methylene chloride or chloroform, in the presence of an acid acceptor such as a nitrogen-containing organic base, for example triethylamine, or in an aqueous-organic medium in the presence of an alkaline condensation agent such as sodium bicarbonate. The reaction temperature is generally between 0° and 40° C.

The product of the general formula (III) in which $R_1$ represents acetoxy is 7-amino-cephalosporanic acid (or 7-ACA) which can be obtained, for example, by the process which forms the subject of Belgian Pat. No. 615,955 or of U.S. Pat. No. 3,239,394.

The products of the general formula (III) in which $R_1$ represents a (5-methyl-1,3,4-thiadiazol-2-yl)-thio, (1-methyl-tetrazol-5yl)-thio or [1-(2-hydroxyethyl)-tetrazol-5-yl]-thio radical and $R_2$ represents a carboxyl radical, or $R_1$ represents a pyridinio radical and $R_2$ the carboxylato ion, can be obtained respectively by the action of 5-methyl-2-thioxo-1,3,4-thiadiazoline, 1-methyl 5-thioxo-tetrazoline, 1-(2-hydroxyethyl)-5-thioxo-tetrazoline or pyridine on a product of the general formula (III) in which $R_1$ represents acetoxy and $R_2$ represents carboxyl. In general, the reaction takes place by heating in an aqueous medium at a temperature of between 40° and 80° C and preferably in the presence of an activator such as an alkali metal iodide or alkali metal thiocyanate, and more particularly potassium thiocyanate.

5-Methyl-2-thioxo-1,3,4-thiadiazoline can be obtained by the method described in Japanese Pat. application No. 72/07,371.

1-Methyl-5-thioxo-tetrazoline can be obtained by the method described by R. STOLLE et al., J. Prakt. Chem. 124, 261 (1930) or R. E. ORTH, J. Pharm. Sci., 52, (9), 909 (1963).

1-(2-Hydroxyethyl)-5-thioxo-tetrazoline can be obtained by the addition reaction of sodium azide with 2-(2-isothiocyanatoethoxy)-tetrahydropyrane. The reaction is generally carried out in an organic solvent such as ethanol, at the reflux temperature of the reaction mixture.

2-(2-Isothiocyanato-ethoxy)-tetrahydropyrane can be obtained by reacting carbon disulphide with 2-(2-aminoethoxy)-tetrahydropyrane in an alkaline medium. The reaction is generally carried out in the presence of sodium hydroxide at the reflux temperature of the reaction mixture.

The acid of the formula (II) can be obtained by one of the following methods:

1. By the action of an ethyl phosphonacetate on 5-oxo-1,3-dithiane in an alkaline medium, followed by the saponification of the resulting mixture of ethyl (1,3-dithiin-5-yl)-acetate and ethyl (1,3-dithian-5-ylidene)-acetate. It is not necessary to purify the mixture of these two isomers in order to carry out the saponification.

In general, ethyl diethoxyphosphonacetate is used and the reaction is carried out in the presence of sodium hydride in an organic solvent such as the dimethyl ether of ethylene glycol, tetrahydrofurane or dimethylformamide, at a temperature of between 10° and 30° C. The saponification is carried out in an alkaline medium, in the presence of sodium hydroxide or potassium hydroxide, in a solvent such as ethanol, at the reflux temperature of the reaction mixture.

2. By the action of ethyl malonate on 5-oxo-1,3-dithiane in a weakly basic medium, followed by hydrolysis and decarboxylation of the mixture of products obtained. The reaction of the ethyl malonate with 5-oxo-1,3-dithiane is generally carried out in an anhydrous organic solvent such as anhydrous tetrahydrofurane in the presence of titanium tetrachloride and of pyridine, at a temperature of between 0° and 30° C. It gives a mixture of ethyl (1,3-dithian-5-ylidene)-malonate and ethyl (1,3-dithiin-5-yl)-malonate, which it is not necessary to purify. The hydrolysis and the decarboxylation are carried out in accordance with the methods usually employed for esters derived from malonic acid, without affecting the remainder of the molecule. This reaction is preferably carried out by heating at a temperature of between 40° and 80° C, in water or in an organic solvent such as ethanol, in the presence of a base such as potassium hydroxide or sodium hydroxide.

5-Oxo-1,3-dithiane can be prepared by the method described by F. G. HOWARD and R. V. LINDSEY, Jr. J.A.C.S. 82, 158 (1960).

According to a further feature of the invention, the compounds of formula (I) in which $R_1$ represents (5-methyl-1,3,4-thiadiazol-2-yl)-thio, (1-methyl-tetrazol-5-yl)-thio or [1-(2-hydroxyethyl)-tetrazol-5-yl]-thio and $R_2$ represents carboxyl, or $R_1$ represents pyridinio and $R_2$ represents the carboxylato ion, are also obtained respectively by the reaction of 5-methyl-2-thioxo-1,3,4-thiadiazoline, 1-methyl-5-thioxo-tetrazoline, 1-(2-hydroxyethyl)-5-thioxo-tetrazoline or pyridine with a product of the general formula (I) in which $R_1$ represents acetoxy and $R_2$ represents carboxyl.

The reaction is generally carried out by heating in an aqueous medium at a temperature of between 40° and 80° C, preferably in the presence of an activator such as an iodide or a thiocyanate and more particularly in the presence of potassium thiocyanate.

The cephalosporin derivatives of the present invention can optionally be purified by physical methods such as chromatography or crystallisation.

The products of the general formula (I) in which $R_2$ represents a carboxyl radical can be converted into metal salts or into addition salts with nitrogen-containing bases in accordance with the methods which are in themselves known. These salts can be obtained, for example, by the action of an alkali metal base or an alkaline earth metal base, ammonia or an amine, on a compound of the general formula (I), in an appropriate solvent such as an alcohol, an ether, a ketone or water, or by an exchange reaction with a salt of an organic acid. The salt formed precipitates, if appropriate after concentrating its solution, and is separated by filtration, decantation or lyophilization. Where a salt is prepared for pharmaceutical purposes, it is, of course necessary to choose a metal cation or cation of a nitrogen-containing base which is pharmaceutically acceptable and non-toxic, i.e., which does not interfere with the formulation and medical use of the active product. Cations which satisfy these conditions are well known.

The cephalosporin derivatives of the present invention exhibit particularly valuable antibacterial properties. They display a remarkable activity, in vitro and in vivo, against Gram-positive and Gram-negative bacteria.

In vitro, the products are active at concentrations of between 0.1 and 0.5 $\mu g/cm^3$ against strains of Staphylococci which are sensitive to penicillin G (Staphylococcus aureus Smith), at concentrations of between 0.25 and 2 $\mu g/cm^3$ against strains of Staphylococci resistant to penicillin G (Staphylococcus aureus MB 9), at concentrations of between 1 and 20 $\mu g/cm^3$ against Escherichia coli Monod strain, and at concentrations of between 4 and 100 $\mu g/cm^3$ against Klebsiella pneumoniae.

In vivo, the new compounds have proved active against experimental infections of mice with Staphylococcus aureus Smith (sensitive to penicillin G) at doses of between 0.5 and 5mg/kg administered subcutaneously or of between 1 and 10 mg/kg administered orally, and experimental infections of mice with Escherichia coli at doses of between 2 and 25 mg/kg administered subcutaneously.

The products of the general formula (I) in which $R_1$ represents a (5-methyl-1,3,4-thiadiazol-2-yl)-thio or (1-methyl-tetrazol-5-yl)-thio radical and $R_2$ represents a carboxyl radical are of particular interest. Amongst these, 2-carboxy-7-(1,3-dithiin-5-yl)-acetamido-3-(1-methyl-tetrazol-5-yl)-thiomethyl-8-oxo-5-thia-1-azabicyclo[4.2.0]oct-2-ene is especially active.

The Examples which follow illustrate the invention.

EXAMPLE 1

(1,3-Dithiin-5-yl)-acetic acid (10 g.) is dissolved in thionyl chloride (50 cc.). The mixture is heated under reflux until the evolution of gas has ceased (about 20 minutes). The brown solution is cooled and concentrated under reduced pressure, the traces of thionyl chloride being entrained, in vacuo, with cyclohexane.

The brown residue obtained is dissolved in methylene chloride (75 cc.) and added, in the course of 30 minutes, to a solution, kept at 0° C, of 3-acetoxymethyl-7-amino-2-carboxy-8-oxo-5-thia-1-aza-bicyclo-[4.2.0.]oct-2-ene (14.1 g.) in methylene chloride (100 cc.) and triethylamine (15.5 cc.). The reaction mixture is then allowed to return to ambient temperature over the course of 2 hours and the methylene chloride is driven off under reduced pressure. The residue is diluted with distilled water (250 cc.) and saturated sodium bicarbonate solution (50 cc.), and the aqueous phase is washed with ethyl acetate (2 × 300 cc.) and then acidified to pH 2 with hydrochloric acid in the presence of ethyl acetate (400 cc.). The aqueous phase is separated and again extracted with ethyl acetate (300 cc). The organic fractions are combined, washed with saturated sodium chloride solution (100 cc.), dried over sodium sulphate, and filtered in the presence of decolorising charcoal. Cyclohexane (1,400 cc.) is added rapidly, while stirring, to the above solution (900 cc.). Stirring is continued for 20 minutes and the suspension obtained is filtered. The solid is washed with a mixture of ethyl acetate and cyclohexane (35:65 by volume, 100 cc.) and then with cyclohexane (100 cc.). The solid is ground in ethyl ether in a mortar, filtered off and then suspended in distilled water (700 cc.) with stirring for 15 minutes. The solid is filtered off and dried under reduced pressure (0.5 mm Hg.). 3-Acetoxymethyl-2-carboxy-7-[(1,3-dithiin 5-yl)-acetamido]-8-oxo-5-thia-1-aza-bicyclo[4.2.0]oct-2-ene (7 g.) is thus obtained in the form of a beige powder $[\alpha]_D^{20} = +79 \pm 1.5°$ (c = 1, dimethylformamide).

(1,3-Dithiin-5-yl)-acetic acid can be prepared by one or other of the following methods A and B.

A. Ethyl diethoxyphosphonacetate (23.4 g.) is added to a suspension of sodium hydride (2.7 g.) in the dimethyl ether of ethylene glycol (200 cc.), while the temperature is maintained at 20° C. 30 minutes after the end of the evolution of gas, 5-oxo-1,3-dithiane (15 g.) dissolved in the dimethyl ether of ethylene glycol (200 cc.) is added over the course of 15 minutes. The temperature rises to 27° C and a gum forms. Stirring is continued for 20 minutes, the mixture is cooled in an ice bath and distilled water (350 cc.) is added. The mixture is extracted with ethyl ether (2 × 300 cc.). The combined organic phases are washed with saturated sodium chloride solution (100 cc.), dried over sodium sulphate, filtered in the presence of decolorizing charcoal, and concentrated under reduced pressure (20 mm Hg).

The residue (25 g.) is mixed with ethyl alcohol (200 cc.) and N sodium hydroxide solution (190 cc.) and heated under reflux for 30 minutes. After cooling, the ethanol is removed under reduced pressure (20 mm Hg). The residue is diluted with water (500 cc.) and the aqueous phase is then brought to pH 1 with 4N hydrochloric acid (60 cc.) in the presence of ethyl acetate (300 cc.). The organic phase is washed with water (200 cc.) and then extracted with saturated sodium bicarbonate solution (3 × 100 cc.). The combined aqueous phases are extracted with ethyl acetate (300 cc.) after having been acidified to pH 1 with 4N hydrochloric acid (50 cc.).

The organic phase is washed with a saturated sodium chloride solution (100 cc.), dried over sodium sulphate, filtered in the presence of decolorizing charcoal, and evaporated to dryness under reduced pressure. A crystalline residue is obtained, which is recrystallised from a mixture of ethyl acetate and cyclohexane (25:75 by volume; 200 cc.). (1,3-Dithiin-5-yl)-acetic acid (11 g.), melting at 97° C, is thus obtained.

B. A solution of titanium tetrachloride (11 cc.) in carbon tetrachloride (25 cc.) is added to anhydrous tetrahydrofurane (200 cc.) kept at 0° C. A solution of ethyl malonate (8 g.) and of 5-oxo-1,3-dithiane (6.7 g.) in anhydrous tetrahydrofurane (50 cc.) is added, over the course of 7 minutes, to the suspension obtained, which is kept at 0° C, and anhydrous pyridine (16 cc.) is then added over the course of 30 minutes while the temperature is allowed to rise to 14° C. The mixture is then stirred for 15 hours at ambient temperature, after which it is poured into water (50 cc.). The mixture is extracted with ether (2 × 50 cc.), and the organic phases are combined, washed with water, dried over magnesium sulphate, and evaporated. The residue is chromatographed over silica gel (125 g.). On eluting with methylene chloride, a light brown oil (10.1 g.) consisting of a mixture of ethyl (1,3-dithian-5-ylidene)-malonate and ethyl (1,3-dithiin-5-yl)-malonate is obtained.

This mixture (10 g.) is dissolved in ethyl alcohol (50 cc.) and potassium hydroxide solution (d = 1.38; 16 cc.) is added to the solution. The mixture is kept at 45° C for 2 hours 30 minutes, cooled and diluted with water (50 cc.). The ethanol is evaporated under reduced pressure and the aqueous phase is washed with ether (3 × 50 cc.) and then acidified with 4N hydrochloric acid (40 cc.). The aqueous phase is extracted with ethyl acetate (3 × 75 cc.) and the combined organic fractions are washed with a saturated sodium chloride solution (75 cc.), dried over magnesium sulphate and evaporated. This gives a residue (6 g.) which is heated in an oil bath at 140° C until the evolution of gas has ceased (about 20 minutes). After cooling, the residue is dissolved in ethyl acetate (50 cc.) and extracted with 20% potassium bicarbonate solution (60 cc.). The aqueous phase is acidified and extracted with ethyl acetate (2 × 50 cc.). The organic fractions are washed, dried over magnesium sulphate, filtered in the presence of decolorising charcoal and evaporated. (1,3-Dithiin-5-yl)-acetic acid (2.8 g.), which after recrystallisation from isopropyl ether melts at 98° C, is thus obtained.

5-Oxo-1,3-dithiane can be prepared by the method described by E. G. HOWARD and R. V. LINDSEY Jr., J. Amer. Chem. Soc. 82, 158 (1960).

EXAMPLE 2

A mixture consisting of 3-acetoxymethyl-2-carboxy-7-[(1,3-dithiin-5-yl)-acetamido]-8-oxo-5-thia-1-aza-bicyclo[4.2.0]oct-2-ene (8.6 g.), distilled water (40 cc.), sodium bicarbonate (3.54 g.), potassium thiocyanate (40 g.) and 5-methyl-2-thioxo-1,3,4-thiadiazoline (2.9 g.) is heated for 6 hours at 60° C. After it has cooled, the mixture is diluted with water (400 cc.) and brought to pH 2.5 with hydrochloric acid. A solid precipitates, the mixture is filtered, the precipitate is washed with water (2 × 100 cc.), dried in vacuo over phosphorus pentoxide and dissolved in acetone (150 cc.). This solution is filtered and the filtrate is added dropwise, with vigrous stirring, to isopropyl ether (600 cc.). The solid which precipitates is filtered off, washed with isopropyl ether (2 × 100 cc.), and dried. 2-Carboxy-7-[(1,3-dithiin-5-yl)-acetamido]-3-[(5-methyl-1,3,4-thiadiazol-2-yl)-thiomethyl]-8-oxo-5-thia-1-aza-bicyclo-[4.2.0]oct-2-ene (3.6 g.) is thus obtained as a beige powder. $[\alpha]_D^{20} = -49.9° \pm 1.1°$ (c = 0.8, dimethylformamide).

Analysis: % calculated: C 40.62; H 3.61; N 11.15; s 31.89. % found: 40.7; 3.8; 10.4; 30.8.

EXAMPLE 3

A mixture of 3-acetoxymethyl-2-carboxy-7-[(1,3-dithiin-5-yl)-acetamido]-8-oxo-5thia-1-aza-bicyclo[4.2.0]-oct-2-ene (11.35 g.), distilled water (50 cc.), sodium bicarbonate (4.9 g.), potassium thiocyanate (50 g.) and 1-methyl-5-thioxo-tetrazoline (3.36 g.) is heated at 60° C for 6 hours. After it has cooled, the mixture is diluted with water (350 cc.) and acidified to pH 2 with hydrochloric acid. The solid which has precipitated is filtered off and washed with water (2 × 200 cc.). The dried solid is dissolved in acetone (60 cc.) and silica gel (20 g.) is suspended in the solution. The mixture is evaporated to dryness and the residue is deposited on a column of silica gel (30 g.). Elution is carried out with ethyl acetate (1.5 liters), fractions of 100 cc. being collected. Fractions 1 to 10 are combined and concentrated to 100 cc. A precipitate then starts to form. Petroleum ether (distillation range 40°–65° C., 200 cc.) is added, and the mixture is stirred vigorously for 5 minutes and is filtered. The precipitate is washed with a mixture of ethyl acetate and petroleum ether (1:2 by volume; 150 cc.) and then with petroleum ether (100 cc.). The solid is suspended in water (150 cc.), and the suspension is stirred vigorously for 15 minutes and filtered. The residue is dried under reduced pressure (0.5 mm Hg). 2-Carboxy-7-[(1,3-dithiin-5-yl)-acetamido]-3-[(1-methyltetrazol-5-yl)-thiomethyl]-8-oxo-5-thia-1-aza-bicyclo-[4.2.0]oct-2-ene (4.2 g.) is thus obtained as a yellow powder, $[\alpha]_D^{20} = -35 \pm 1°$ (c = 0.8, dimethylformamide)

Analysis: % calculated: C 39.42; H 3.73; N 17.27; S 26.36. % found: 39.2; 3.9; 15.7; 25.9.

The present invention also provides pharmaceutical compositions, usable in therapy, which contain a compound of the formula (I) or, where appropriate, one of its salts as aforesaid, as the active product, in association with one or more pharmaceutically acceptable diluents or adjuvants. The compositions can in particular be formulated for parenteral use.

Compositions for parenteral administration can be sterile aqueous or non-aqueous solutions, suspensions or emulsions. As the solvent or vehicle, sterile, pyrogen-free water, propylene glycol, polyethylene glycol, vegetable oils, in particular olive oil, and injectable organic esters, for example ethyl oleate, can be employed. These compositions can also contain adjuvants, in particular wetting agents, emulsifiers or dispersing agents. Sterilization can be carried out in various ways, for example with the aid of a bacteriological filter, by incorporating sterilizing agents into the composition, or by irradiation.

The compositions can also be prepared in the form of sterile solid compositions which can be dissolved, at the time of use, in sterile water or in any other injectable sterile medium.

Such compositions for parenteral use generally contain from 0.01 to 20% by weight of the active compound in the sterile injectable medium.

In human therapy, the compositions according to the invention are particularly useful in the treatment of infections of bacterial origin.

In general terms, the physician decides the posology which he considers to be the most appropriate, as a function of the age, the weight, the degree of infection and other factors specific to the subject to be treated. In general, the doses are between 1 and 12 g. of active product per day, administered intramuscularly or intravenously, for an adult.

The Example which follows illustrates a composition according to the invention.

EXAMPLE 4

An injectable solution having the following composition is prepared:

| | |
|---|---|
| Sodium salt of 2-carboxy-7-(1,3-dithiin-5-yl)-acetamido-3-(1-methyl-tetrazol-5-yl)-thiomethyl-8-oxo-5-thia-1-aza-bicyclo[4.2.0]oct-2-ene | 261.5 mg. |
| Sodium chloride | 1.6 mg. |
| Injectable solvent | 2 cc. |

We claim:

1. Cephalosporin derivatives of the formula:

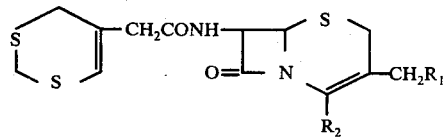

in which $R_1$ represents acetoxy, (5-methyl-1,3,4-thiadiazol-2-yl)-thio, (1-methyl-tetrazol-5-yl)-thio or [1-(2-hydroxyethyl)-tetrazol-5-yl]-thio and $R_2$ represents carboxyl, or $R_1$ represents pyridinio and $R_2$ the carboxylato ion, and, when $R_2$ represents carboxyl, their salts with non-toxic metals and addition salts with non-toxic nitrogen-containing bases.

2. A compound according to claim 1 which is 3-acetoxymethyl-2-carboxy-7-[(1,3-dithiin-5-yl)acetamido]-8-oxo-5-thia-1-azabicyclo[4.2.0]oct-2-ene and its salts with non-toxic metals and non-toxic nitrogen-containing bases.

3. A compound according to claim 1 which is 2-carboxy-7-[(1,3-dithiin-5-yl)acetamido]-3-[(5-methyl-1,3,4-thiadiazol-2-yl)thiomethyl]8-oxo-5-thia-1-aza-bicyclo[4.2.0]-oct-2-ene and its salts with non-toxic metals and non-toxic nitrogen-containing bases.

4. A compound according to claim 1 which is 2-carboxy-7-[(1,3-dithiin-5-yl)acetamido]-3-[(1-methyltetrazol-5-yl)thiomethyl]-8-oxo-5-thia-1-aza-bicyclo[4.2.0]-oct-2-ene and its salts with non-toxic metals and non-toxic nitrogen-containing bases.

5. A antibacterial pharmaceutical composition comprising a cephalosporin derivative as claimed in claim 1 or when $R_2$ is carboxy or a salt thereof with a pharmaceutically acceptable, non-toxic metal or with a pharmaceutically acceptable, non-toxic nitrogen-containing base, in association with a compatible pharmaceutically acceptable diluent or adjuvant.

6. A method of treating a bacterial infection which comprises administering to a subject suffering therefrom an effective amount of a cephalosporin derivative as claimed in claim 1.

* * * * *